US008571622B2

(12) United States Patent
Huiku et al.

(10) Patent No.: US 8,571,622 B2
(45) Date of Patent: Oct. 29, 2013

(54) METHOD FOR REDUCING POWER CONSUMPTION IN PULSE OXIMETER SYSTEMS, PULSE OXIMETER SYSTEM AND PULSE OXIMETER SENSOR

(75) Inventors: Matti Huiku, Espoo (FI); Juha Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 729 days.

(21) Appl. No.: 12/872,078

(22) Filed: Aug. 31, 2010

(65) Prior Publication Data
US 2012/0053432 A1    Mar. 1, 2012

(51) Int. Cl.
*A61B 5/00*    (2006.01)

(52) U.S. Cl.
USPC ........................................................ 600/324

(58) Field of Classification Search
USPC ........................................................ 600/324
See application file for complete search history.

(56) References Cited

U.S. PATENT DOCUMENTS

| | | | | |
|---|---|---|---|---|
| 4,510,940 | A * | 4/1985 | Wesseling | 600/480 |
| 6,261,236 | B1 * | 7/2001 | Grimblatov | 600/500 |
| 6,697,655 | B2 * | 2/2004 | Sueppel et al. | 600/322 |
| 7,499,740 | B2 | 3/2009 | Nordstrom et al. | |
| 2004/0039273 | A1 * | 2/2004 | Terry | 600/322 |
| 2004/0147850 | A1 * | 7/2004 | Amano et al. | 600/513 |
| 2006/0122476 | A1 * | 6/2006 | Van Slyke | 600/336 |
| 2007/0129617 | A1 * | 6/2007 | Noel et al. | 600/323 |
| 2008/0183232 | A1 * | 7/2008 | Voss et al. | 607/24 |
| 2011/0125033 | A1 * | 5/2011 | Saito et al. | 600/485 |
| 2011/0270058 | A1 * | 11/2011 | Price et al. | 600/324 |

OTHER PUBLICATIONS

"Heart Rate and Blood Pressure Estimation from Compressively Sensed Photoplethysmograph", Baheti et al., BodyNets 2009, Fifth Int'l. Conference on Body Area Networks, UCLA (Los Angeles, CA, Apr. 1-3, 2009.
"An ultra low power pulse oximeter sensor based on compressed sensing", Baheti et al., BSN 2009, Body Sensor Networks Conference, Berkeley, CA, Jun. 3-5, 2009.
"Packet Loss Mitigation for Biomedical Signals in Healthcare Telemetry", Garudadri et al., 31st Annual Int'l Conference of the IEEE EMBS, Minneapolis, MN, USA, Sep. 2-6, 2009.

* cited by examiner

*Primary Examiner* — Rodney Fuller
(74) *Attorney, Agent, or Firm* — Andrus, Sceales, Starke & Sawall, LLP

(57) ABSTRACT

Method and pulse oximeter system for determining blood characteristics of a subject are disclosed. A pulse oximeter sensor for collecting plethysmographic data is also disclosed. In order to reduce the power consumption, time instants of systolic rises are estimated in at least one plethysmographic waveform of a subject and light emitting elements of a sensor are controlled according to the estimated time instants, thereby to collect signal samples from a plurality of plethysmographic waveforms of the subject during the systolic rises. A desired blood parameter, typically oxygen saturation, is then defined based on the signal samples collected during the systolic rises.

20 Claims, 5 Drawing Sheets

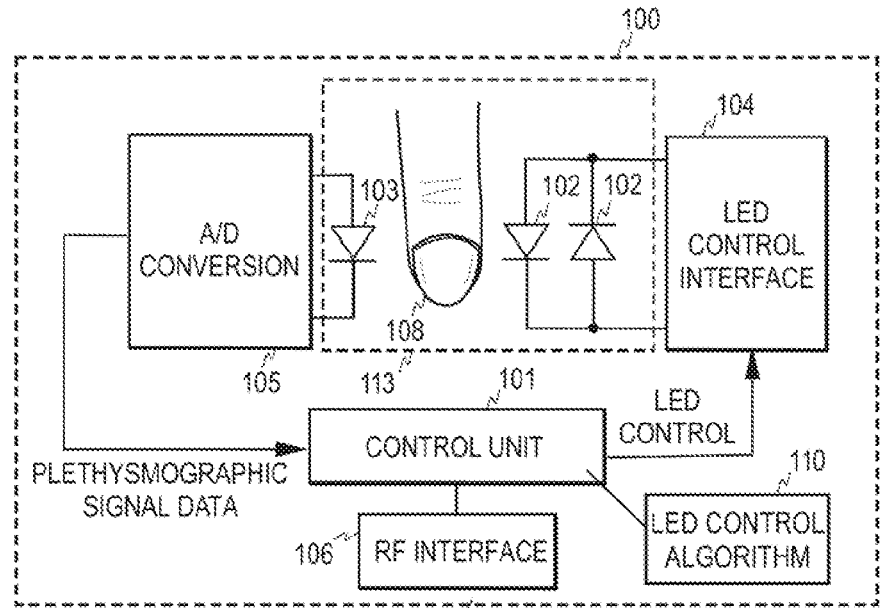
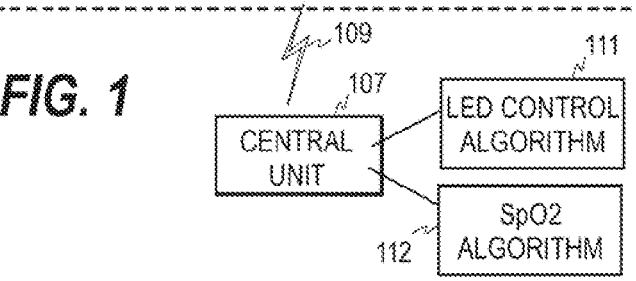
FIG. 1
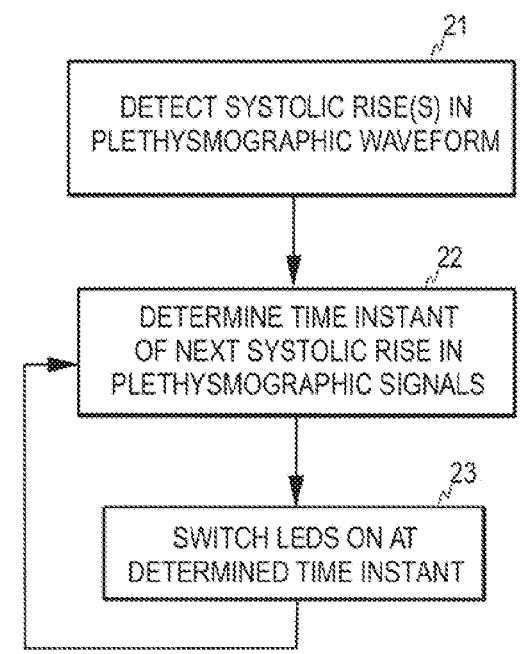
FIG. 2

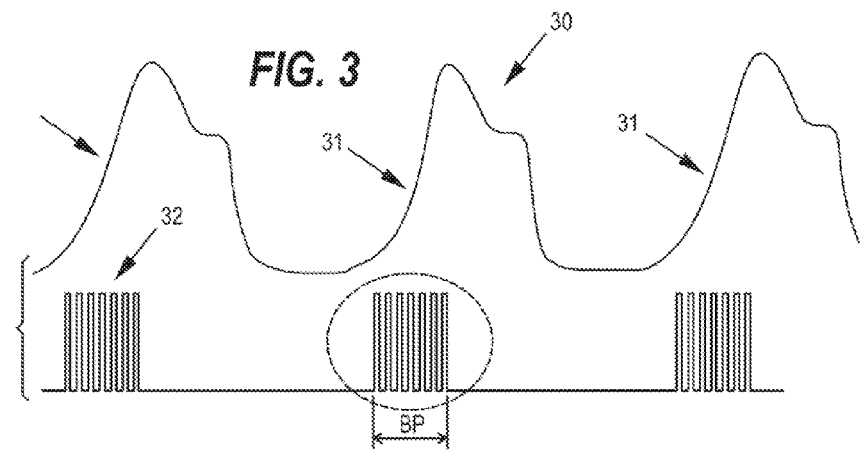
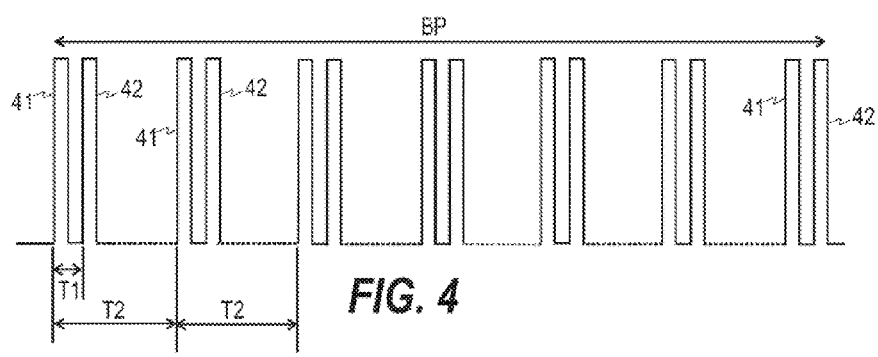
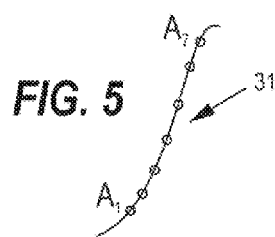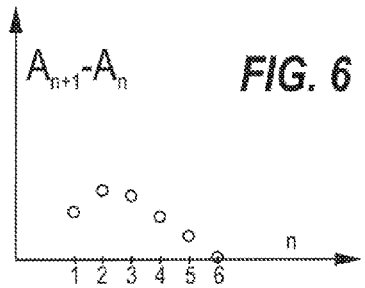
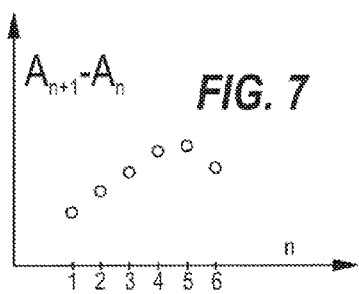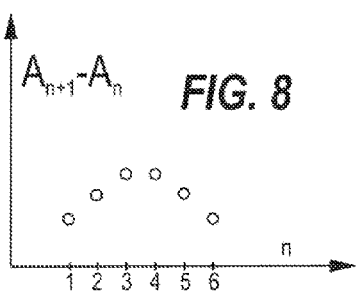

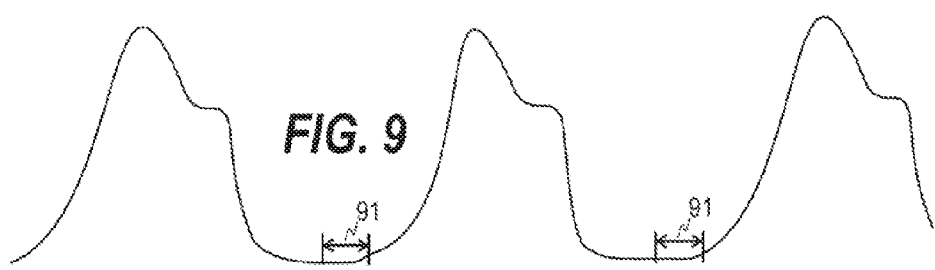
FIG. 9
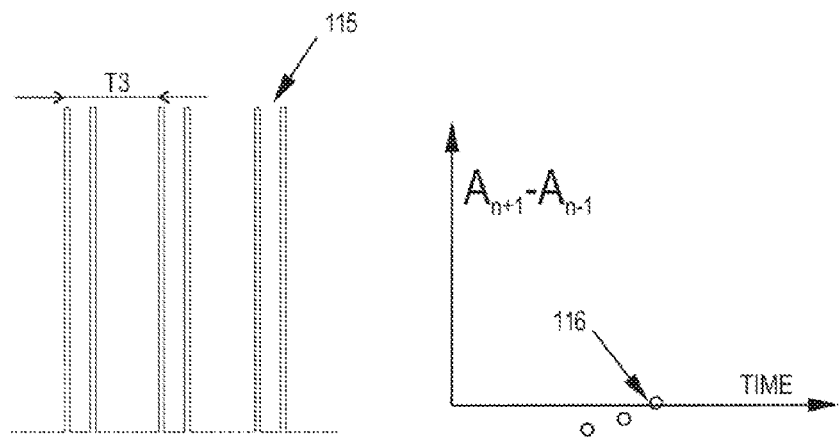
FIG. 10
FIG. 11
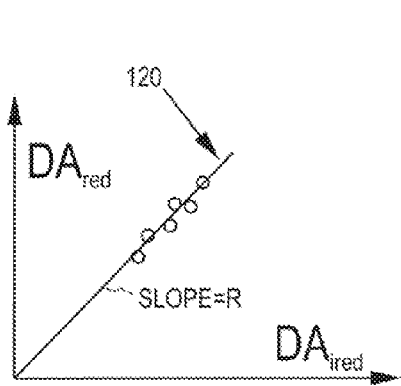
FIG. 12
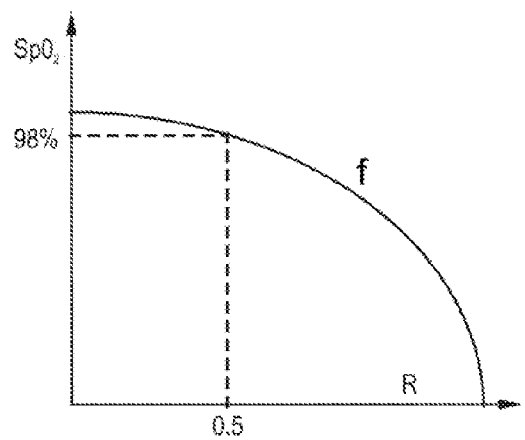
FIG. 13

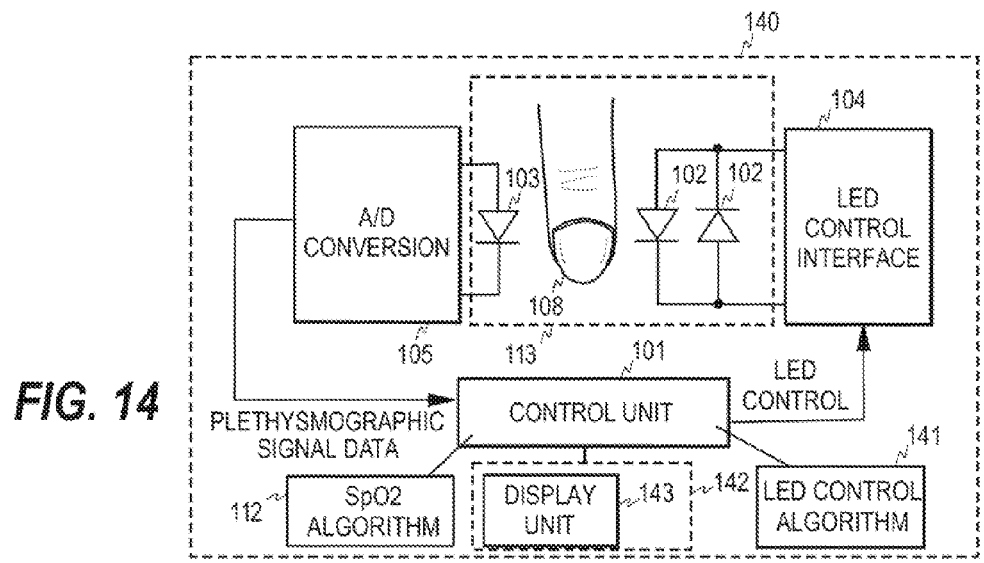
FIG. 14
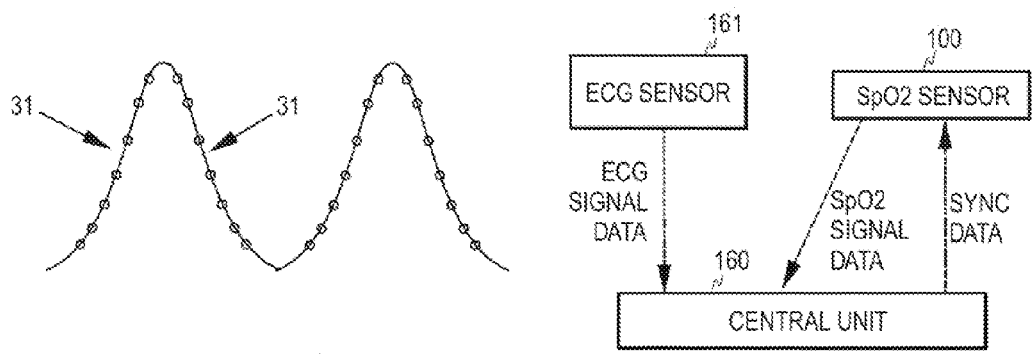
FIG. 15
FIG. 16
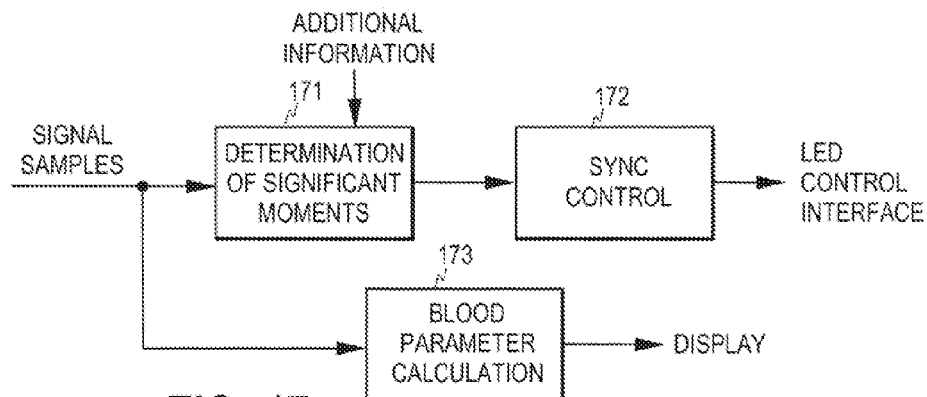
FIG. 17

METHOD FOR REDUCING POWER CONSUMPTION IN PULSE OXIMETER SYSTEMS, PULSE OXIMETER SYSTEM AND PULSE OXIMETER SENSOR

BACKGROUND OF THE INVENTION

This disclosure relates generally to pulse oximeters. More particularly, this disclosure relates to techniques for reducing power consumption in pulse oximeters, especially in battery operated pulse oximeter sensors. A pulse oximeter sensor here refers to a pulse oximeter unit provided with optical components, i.e. light emitting elements and one or more photodetectors, for collecting (photo)plethysmographic signal data. The sensor may be a single element or comprise a base unit and a separate optical unit that may be attached to a subject and connected to the base unit.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters provide instantaneous in-vivo measurements of arterial oxygenation, and thereby an early warning of arterial hypoxemia, for example. Pulse oximeters also display a photoplethysmographic (PPG) pulse waveform, which can be related to tissue blood volume and blood flow, i.e. the blood circulation, at the site of the measurement, typically in finger or ear.

At present, there is a growing interest to develop portable and wearable medical sensors for various medical applications that allow the subject to move freely and thus also remote supervision of the subject. Wireless Body Area Network (WBAN) refers to short-range radio-frequency communications technologies, which are specifically suited for transmitting measurement data between different patient-worn devices. In a typical set up, multiple tiny, battery-operated sensors (e.g. ECG patch on chest and SpO2 clip on finger) send measurement data to a patient-worn central unit. The central unit may be a small monitor by itself, including a display and even alarming functionality. The central unit may also communicate the measurement data and analysis results to a hospital-wide network using building-wide radio-frequency communications technologies, such as WiFi. Although WBAN technology is still in its infancy, WBAN applications are expected to increase drastically in the near future.

Low power consumption is a pre-requisite for WBAN sensors, and generally for all wearable or implanted sensors. As to pulse oximeters, the power consumption is largely due to the power requirement of the light sources (LEDs), which are normally driven continuously at a high rate. Therefore, techniques have been developed for reducing the power consumption of the LEDs. These techniques are based on reduction of the amplitude and/or width of the LED pulses, thereby to reduce the energy of the pulses. However, as the signal-to-noise ratio cannot be dropped below a certain threshold level, which may vary in different measurement environments, the reduction is normally accompanied with a noise measurement, so that the signal-to-noise ratio does not drop too low.

After today's advanced power reduction techniques have been taken into use, the power consumption of the pulse oximeter sensor is still around 20 mW. In a small finger clip type pulse oximeter sensor a suitable battery could be, for example, an LR44 coin cell. The voltage of such a battery is 1.5 V and the capacity 150 mAh, i.e. 220 mWh. That is, the battery provides about 10 hours of operating time with the above-mentioned power consumption. Consequently, the battery needs to be changed rather frequently, which is not only disturbing but may also cause a break in the measurement, especially in environments where the nursing staff is not constantly available for a battery change.

Lower power consumption levels have been reported in pulse oximeter sensors based on so-called compressed sensing. In these sensors, the plethysmographic signal data is acquired at a low sampling rate (i.e. LED blinking rate), which is below the Nyquist rate. This, however, increases the complexity of the signal processing needed to reconstruct the signal. Further, the more the sampling rate is below the Nyquist rate, the longer the signal sequence needed to reconstruct the signal. Consequently, the measurement slows down and an SpO2 value is not obtained for each cardiac cycle. Furthermore, reconstruction algorithms based on sub-Nyquist sampling are always based on assumptions about the amplitude and frequency content of the signal and noise. Hence, if the signal-to-noise ratio drops too low, this kind of reconstruction algorithms become unreliable.

Although the power consumption of a pulse oximeter sensor is largely due to the power requirement of the LEDs, the data transmission may also consume a considerable part of the power budget, at least if retransmissions are required frequently due to collisions, for example. It is generally thought that each sensor in a body area network samples and sends out data independently. In practice, it is, however, beneficial to synchronize the data transmission in order to minimize the number of collisions. For this purpose, a return data path is implemented. Hence, two-way communication and synchronization mechanisms are in place in body area networks. Data is typically sent in bursts with a typical interval of 50 to 1000 ms. Considering the power consumption, it is beneficial to increase the packet size, thereby to reduce the relative amount of overhead information to be transmitted. In case of signals with relatively high data rate, the data packet interval is usually short by nature. For example, for ECG measurement a packet interval of about 50 ms is appropriate, whereas temperature measurement data need not to be transmitted more frequently than about once in a second. As to pulse oximeters, the amount of data to be transmitted is normally rather small and thus the interval between data packets may be rather long.

Further, the development of pulse oximeters brings along new applications and higher performance. However, a pre-requisite for the introduction of new features and higher performance is an increased number of light sources in the pulse oximeter. When battery operability is required from the sensor, the power consumption issue is therefore even more essential in these new multi-wavelength pulse oximeters.

Consequently, in order to enhance the operating time of battery-operated pulse oximeter sensors and the fluency of continuous and long-term monitoring, it is desirable to provide pulse oximeter sensors that consume less power without compromising the quality and swiftness of the actual measurement and without adding complexity to the processing of the acquired plethysmographic signal data. Given the trend towards body area networks, it would also be beneficial if the power consumption of the pulse oximeter sensor could be reduced not only in terms of the LED operation but also in terms of the data transmission.

BRIEF DESCRIPTION OF THE INVENTION

The above-mentioned problems are addressed herein which will be comprehended from the following specification. In order to reduce the power consumption of a pulse oximeter sensor, the time instants of the systolic rises of the plethysmographic waveforms are estimated and the light emitting elements are energized so that plethysmographic signal data is collected only from limited waveform sections that include the systolic rises. These sections of the plethysmographic waveforms carry all the information needed for the SpO2 measurement and the SpO2 values may thus be derived from these waveform sections only. The plethysmographic waveform here refers to the signal waveform obtained at a specific wavelength, and thus at least two waveforms (wavelengths) are needed to obtain SpO2 values. Although SpO2 is a typical example of a blood parameter to be derived from the collected photoplethysmographic data, any blood parameter may in principle be determined, for which the collected signal sections provide enough input data. One such blood parameter may be hemoglobin (Hb). However, SpO2 is in this context used as an example of the blood parameter to be determined, since it is the universal blood parameter determined by pulse oximeters.

In an embodiment, a method for determining blood characteristics of a subject based on photoplethysmographic data comprises estimating time instants of systolic rises in at least one plethysmographic waveform of a subject, controlling light emitting elements of a sensor according to the estimated time instants, thereby to collect signal samples from a plurality of plethysmographic waveforms of the subject during the systolic rises, and defining at least one desired blood parameter based on the signal samples collected during the systolic rises.

In another embodiment, a pulse oximeter system for determining blood characteristics of a subject based on photoplethysmographic data comprises a sensor comprising light emitting elements and a first synchronization unit configured to estimate time instants of systolic rises in at least one plethysmographic waveform of a subject. The pulse oximeter system further comprises a second synchronization unit configured to control the light emitting elements according to the estimated time instants, thereby to collect signal samples from a plurality of plethysmographic waveforms of the subject during the systolic rises and a calculation unit configured to define at least one desired blood parameter based on the signal samples collected during the systolic rises.

In still another embodiment, a pulse oximeter sensor for collecting plethysmographic data comprises light emitting elements and a synchronization unit configured to receive timing information indicative of time instants of systolic rises in plethysmographic waveforms of a subject and to control the light emitting elements according to the time instants, thereby to collect signal samples from the plethysmographic waveforms during the systolic rises.

Various other features, objects, and advantages of the invention will be made apparent to those skilled in the art from the following detailed description and accompanying drawings.

BRIEF DESCRIPTION OF THE DRAWINGS

FIG. 1 illustrates one embodiment of pulse oximeter system with reduced power consumption;

FIG. 2 is a flow diagram illustrating one embodiment for collecting plethysmographic data;

FIG. 3 illustrates the timing of the LED bursts with respect to the plethysmographic waveform signal;

FIG. 4 illustrates an example of the LED bursts of FIG. 3;

FIG. 5 illustrates the samples obtained from the systolic rise of the plethysmographic waveform signal;

FIGS. 6 to 8 illustrate one embodiment for maintaining synchronization between the plethysmographic waveforms and the LED pulses;

FIGS. 9 to 11 illustrate another embodiment for maintaining synchronization between the plethysmographic waveforms and the LED pulses;

FIG. 12 illustrates one embodiment for calculating the SpO2 value based on the samples obtained during one cardiac cycle;

FIG. 13 illustrates the calibration curve of a pulse oximeter;

FIG. 14 illustrates a single device pulse oximeter system;

FIG. 15 illustrates another embodiment for calculating the SpO2 values;

FIG. 16 illustrates a body area network provided with a pulse oximeter;

FIG. 17 illustrates an example of the functional entities of a pulse oximeter system.

DETAILED DESCRIPTION OF THE INVENTION

Figure 18:
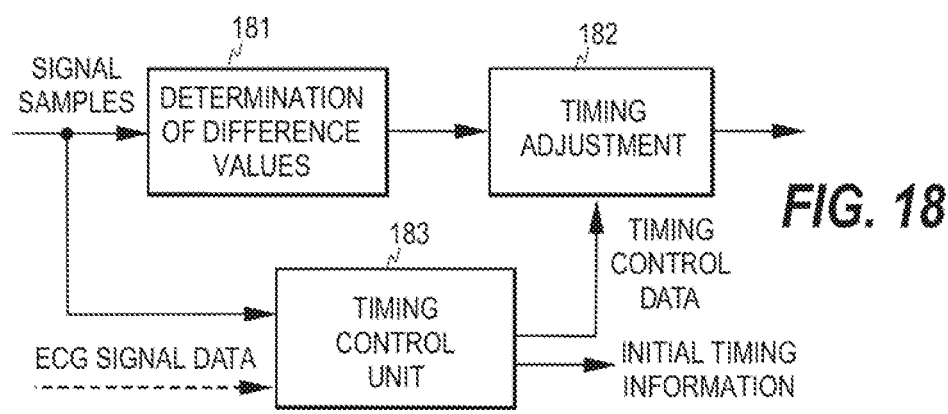
FIG. 18 illustrates an example of the functional entities of a pulse oximeter system in terms of LED synchronization.

FIG. 1 illustrates one embodiment of a low power pulse oximeter system. The system comprises a smart sensor 100 attachable to a subject and a central unit 107 adapted to communicate with the smart sensor. The smart sensor normally includes two or more light emitting elements, such as LEDs, and at least one photodetector 103. It is assumed here that the smart sensor includes two LEDs 102, each emitting light at a dedicated wavelength. The wavelength values widely used are 660 nm (red) and 940 nm (infrared). The light emitted by the LEDs and propagated through (or reflected from) the tissue, such as finger 108, is received by the photodetector 103 which converts the optical signal received at each wavelength into an electrical signal.

The smart sensor further comprises a control unit 101, such as a microcontroller, that controls the LEDs through a LED control interface 104, and an A/D converter 105 that converts the electrical signal obtained from the photodetector into digitized format. The control unit receives the (photo)plethysmographic signal data from the A/D converter, and there may also be an amplifier between the photodetector and the control unit. The control unit is connected to a radio frequency interface 106 for transmitting the plethysmographic signal data to the central unit 107 and for receiving data from the central unit. Thus, it is assumed here that there is a two-way communication link 109 between the smart sensor and the central unit.

For controlling the LEDs, the control unit 101 is provided with a LED control algorithm 110 configured to control, when executed by the control unit, the LEDs 102 through the LED control interface 104. The central unit 107 is provided with a LED control algorithm 111 that co-operates with algorithm 110, and with an SpO2 calculation algorithm 112. The algorithms 110 and 111 handle the synchronization of the LED operation with the plethysmographic waveforms and the SpO2 calculation algorithm 112 is configured to determine the SpO2 values.

In various embodiments of the pulse oximeter system, plethysmographic signal data is collected only during certain waveform sections that include the systolic rises of the plethysmographic waveforms. Therefore, during the recording of the data the LEDs may be switched on during the said sections only. In some embodiments of the system, however, the LEDs may also be used to synchronize the data collection with the systolic rises. The functionalities of the LED control algorithm 110 depend on the synchronization mechanism and on how the synchronization functionalities are divided between the sensor and the central unit, i.e. between algorithms 110 and 111.

In practice, the smart sensor of FIG. 1 may be divided into two different units; a sensor 113 comprising the optical components of a conventional sensor, i.e. LEDs 102 and photodetector 103, and a base unit comprising the non-optical components of the smart sensor 100. The sensor 113, which is attachable to the subject, may be connected through a short cable to the base unit. In this way, the smart sensor may be divided between a disposable unit, i.e. sensor 113, and a unit with longer durability, i.e. the base unit.

FIG. 2 illustrates one embodiment of a method for collecting plethysmographic signal data in the smart sensor of FIG. 1. Before the actual SpO2 measurement is started, at least one plethysmographic waveform signal is recorded over at least one cardiac cycle, thereby to detect the systolic rise(s) in the said cycle(s) (step 21). This initial detection step may be carried out by switching one or more LEDs on at normal high rate for a given time period, thereby to obtain plethysmographic waveform data over at least one cardiac cycle at at least one wavelength. The time instant of each systolic rise may then be determined by finding out the maximum derivative within each cycle, for example. The maximum derivative corresponds substantially to the midpoint of the systolic rise. The time instant here refers to any one or more time values that indicate when a systolic rise occurs in the plethysmographic waveforms. The time instants of the systolic rises may also be determined by determining the periods within which the rises occur. It is to be noted here that the initial detection step 21 is typically carried out at one wavelength only, since one waveform is enough for the determination of the time instants of the systolic rises, while the actual data collection is typically carried out at all wavelengths.

Upon carrying out the initial detection step 21, the actual data collection may start. Based on the time instant(s) determined at step 21, the time instant of next systolic rise is determined/predicted in step 22 and the LEDs are switched on so that the LED pulses hit the systolic rise of the waveforms (step 23). Steps 22 and 23 are then repeated to collect plethysmographic signal data from the systolic rises only or from waveform sections including the systolic rises. The plethysmographic data is thus collected only from specific parts of the (photo)plethysmographic signal, i.e. from waveform sections including the systolic rises.

FIG. 3 illustrates one embodiment of the data collection process of steps 22 and 23. The figure shows a typical waveform 30 of the plethysmographic signal during three successive cardiac cycles. Each cycle comprises a systolic period and a subsequent diastolic period, which result from the pumping operation of the heart. The systolic period consists of systolic rises 31 that are produced when the heart is contracting. Given that the length of one cardiac cycle is normally about 1 Hz, the length of the systolic rise is about 100 ms, while the length of the diastolic period is about 900 ms. When the heart rate varies, the length of the systolic rise does not change significantly. Instead, the heart rate variation is reflected in the length of the diastolic period and thus it is mainly the diastolic period that varies when the heart rate varies. During the collection of the plethysmographic data, the LEDs are switched on so that a light burst 32 hits each systolic rise of each plethysmographic waveform.

In FIG. 3, it is assumed that a light burst 32 comprises seven successive measurement slots in which the LEDs of the sensor are ignited. FIG. 4 shows an example of one light burst 32 circled in FIG. 3. In this example, each of the seven measurement slots comprises two successive pulses 41, 42, one pulse being a red pulse and the other an infrared pulse. The width of each LED pulse is typically between 20 and 100 microseconds, while the length T1 between two successive pulses may be between 100 and 200 microseconds, for example. The length T2 of one measurement slot is typically from 2.5 to 10 milliseconds. The number of measurement slots, i.e. red-infrared pulse pairs, within one light burst varies typically from 7 to 10. It is assumed here that seven pulse pairs are generated for each systolic rise, as is shown in FIGS. 3 and 4 (where the systolic rise refers generally to the systolic rise of both wavelengths).

FIG. 5 illustrates the seven samples $A_1$ to $A_7$ obtained during one systolic rise 31 of the signal at each wavelength. To obtain the samples from the systolic rises, the control of the LEDs has to remain synchronized with the systolic rises. To this end, different synchronization mechanisms may be used. It is assumed here that initially the systolic rises are detected similarly as is discussed in connection with step 21 of FIG. 2.

FIGS. 6 to 8 illustrate one synchronization maintenance mechanism in which six difference values $A_{n+1}-A_n$ (n=1, . . . , 6) are calculated based on the seven signal values $A_1$-$A_7$ obtained at each wavelength from each systolic rise. The control unit (or the central unit) calculates the six difference values and compares their mutual magnitudes. If the midmost difference values are the greatest ones, as is the case in FIG. 8, the light burst is at an appropriate temporal position in relation to the signal waveform. If the smallest difference values are obtained at the end of the light burst, the burst is late and the period between the bursts should be shortened. This case is illustrated in FIG. 6. If the smallest difference values are obtained at the beginning of the light burst, the burst is early and the period between the bursts should be lengthened. This case is illustrated in FIG. 7. By examining the difference values in the above-described mariner, the control unit (or the central unit) may adjust the time period between the light bursts and keep the light bursts synchronized with the signal waveforms, so that the light bursts hit the systolic rises of the plethysmographic waveforms as accurately as possible.

FIGS. 9 to 11 illustrate another embodiment for maintaining synchronization between the light bursts and the plethysmographic waveforms. In this embodiment, one of the LEDs is controlled to start sending test pulse pairs well before the systolic rise is expected to start. A difference value is derived from each test pulse pair to detect the start of a systolic rise in the signal. FIG. 9 illustrates the test periods 91 during which test pulse pairs are sent, while FIG. 10 illustrates three successive test pulse pairs 115. The interval T3 between two successive test pulse pairs may be, for example, about 30 milliseconds. FIG. 11 shows an example of the difference values obtained from the test pulse pairs. In this example, the third test pulse pair yields a positive value 116 and the sending of the light burst 32 may thus be triggered at this time instant. The test pulse pairs are sent in each cardiac cycle to detect the start of the systolic rise within each cycle.

To maintain synchronization, the initial detection step 21 may also include producing and initializing an autoregressive model based on a plurality of time instants determined over a corresponding plurality of cardiac cycles. In step 22, the next time instant of a systolic rise may then be predicted based on preceding time instants or time differences, i.e. new parameters may be input to the model every cardiac cycle.

In the above embodiments, the synchronization is obtained and maintained based on the same signal(s) to which the LED pulses are synchronized. The synchronization signal, i.e. the LED control data, may be generated in the smart sensor or in the central unit. If the synchronization signal is generated in the central unit, the smart sensor may send the signal samples or the difference values to the central unit and the central unit may then determine the time instants of the LED bursts and control the LEDs over the communication link 109.

Based on the seven samples (or the respective six difference values), the SpO2 value may be determined. This may be carried out in the central unit (algorithm 112), since the supervising is normally carried out at the central unit. FIG. 12 illustrates one embodiment for calculating the SpO2 values, which is based on linear regression. In the example of FIG. 12, the infrared differential $DA_{ired}$ is used as the explanatory variable and the red differential $DA_{red}$ as the dependent variable (where $DA=A_{n+1}-A_n$). A linear regression fit is used to find out the best fit line 120 that goes through the origo. The slope of the line represents the known pulse oximeter ratio R. As is known, pulse oximeters use an empirically determined calibration curve f, shown in FIG. 13, to transform the R values into $SpO_2$ percentages (SpO2=f(R)). Consequently, the SpO2 value is obtained by determining the slope of the best fit line 120 and using the calibration curve f to transform the slope value to an SpO2 percentage. In this way, an SpO2 value is obtained for each cardiac cycle.

Depending on the implementation, the difference values DA may be calculated in the smart sensor or in the central unit. If the difference values are calculated in the smart sensor, the sensor may maintain the synchronization with the plethysmographic waveforms without the assistance of the central unit. However, the central unit may also send timing information to the smart sensor. Regardless of how the synchronization is implemented, the determination of the SpO2 values is normally carried out in the central unit 107 (algorithm 112).

In the embodiment of FIG. 1, the pulse oximeter system comprises a smart sensor 100 and a separate central unit 107, where the smart sensor may be a single unit or divided between a sensor provided with the optical components of the smart sensor and a base unit provided with the non-optical components of the smart sensor. FIG. 14 illustrates another embodiment of the pulse oximeter system, in which all components are integrated into a single device 140. The device comprises the same elements as the embodiment of FIG. 1, except that the RF interface is now omitted and the device is provided with complete LED control and SpO2 algorithms 141 and 112, respectively, as the device determines the SpO2 value without the help of an external unit. Like reference numerals are used as in FIG. 1 to indicate like parts. Instead of the RF interface, the device is now provided with a limited user interface 142 for operating the device. The user interface includes a small low-power display unit 143. The control unit controls the display to present the SpO2 values on the screen of the display. The device of FIG. 14 may be used as a spot-checker that can be carried in a pocket, for example. Low power consumption is an essential feature for such portable devices, and thus the device benefits from the LED synchronization mechanism described above.

The SpO2 values may also be calculated in frequency domain by subjecting the values obtained from the systolic rises to a Fourier transform. The values are put in succession, i.e. the gaps in the waveforms are omitted, and the transform is performed for each wavelength, or for at least the red and infrared wavelengths. The spectrum peaks that correspond to the systolic rise time in the red and infrared spectra are then found out. The numeric value of the ratio R may be obtained through the equation $R=sqrt(PSD(AC_{red}/DC_{red})/PSD(AC_{ired}/DC_{ired}))$, where sqrt refers to square root and PSD $(AC_{red}/DC_{red})$ is the red spectrum peak that corresponds to the systolic rise time and $PSD(AC_{ired}/DC_{ired})$ the infrared spectrum peak that corresponds to the systolic rise time. The SpO2 values are then obtained through the calibration curve f by determining the SpO2 percentage that corresponds to the R value.

In another embodiment, the values obtained from the systolic rises are not simply put one after another as above, but every second systolic rise is converted to its mirror image before the samples are put in succession. A signal sequence obtained is illustrated in FIG. 15. Mirror imaging the samples of every second systolic rise facilitates the detection and removal of interferences, such as respiration modulation and baseline fluctuation caused by non-ideal synchronization of the sampling with the systolic rises. The signal sequence is supplied to the Fourier transform and SpO2 values are calculated as discussed above. Instead of converting every second systolic rise to its mirror image, the samples of each systolic rise can be used twice: first in correct order and then in inverted order, or vice versa. This is typically carried out in the central unit, so that the smart sensor can operate as if no doubling of the data points were made.

The synchronization may also be obtained from an ECG signal measured from the subject. FIG. 16 illustrates an example, in which a common central unit 160 receives plethysmographic signal data from a pulse oximeter sensor 100 and ECG signal data from an ECG sensor 161. In this example, the synchronization may be carried out through the R peaks of the ECG signal. Initially, the LEDs may be switched on at the normal high rate, thereby to obtain the plethysmographic waveforms during at least one cardiac cycle. Based on this data and the ECG signal data measured from the ECG sensor, the central unit 160 may measure the pulse transit time (PTT) for example by measuring the time instant of the R peak and the time instant of the maximum derivative of the PPG waveform and then subtracting the obtained ECG peak time from the obtained PPG time. When the SpO2 measurement starts, the central unit may first detect the R peaks from the received ECG signal data, measure the PTT, and generate a synchronization signal according to the time instant of each R peak and the measured PTT value. Since the ECG sensor typically sends ECG signal data frequently, such as every 50 milliseconds, and since the PTT is greater than the interval between the ECG packets, it is possible to implement direct triggering of oximetry data sampling in body area networks. That is, the central unit may define the LED burst time based on the R peak time and the PTT and send the timing information to the smart sensor before the systolic rise that corresponds to the R peak appears in the plethysmographic waveform. ECG-based synchronization is particularly beneficial whenever the heart rate variability (HRV) is large. This is the case for example when the patient suffers from atrial fibrillation. In this case accurate prediction of the next systolic rise is not possible based on the plethysmographic signals alone, because the R-R period varies randomly from one heart beat to another. However, even in case of large HRV, the PTT remains relatively constant. This means that the timing of the LED burst can be accurately adjusted for each heart beat based on the time of the R peak.

In one embodiment of ECG based synchronization, the PTT needs not to be determined. Instead, the LEDs are pulsed (at the normal high rate) for a given time period after each R peak detected. This time period is long enough, such as 200 ms, to cover the systolic rise corresponding to each R peak. Thus, in this embodiment a coarse estimation of the time instants of the systolic rises is carried out based on the R peaks only, i.e. completely without the plethysmographic data. This is not as efficient as measuring the PTT and adjusting the LED burst time and duration for the individual patient. However, even this LED burst of constant duration provides significant power saving compared to continuous sampling.

FIG. 17 illustrates an example of the functional entities of a pulse oximeter system. The synchronization operations may be divided into two operational entities: a first synchronization unit 171 configured to estimate the significant moments of the plethysmographic waveform, i.e. the moments of LED activation, and a second synchronization unit 172 configured to control the LEDs accordingly. The system further comprises a calculation unit 173 configured to calculate the blood parameter values, typically SpO2 values, based on the incoming signal samples. Apart from the signal sampled, the first synchronization unit 171 may receive various additional information that may be used to generate the timing information (LED control data). This input information may include, for example, ECG signal data that allows the calculation of the pulse transit time value. The pulse transit time may be determined regularly, thereby to keep the light bursts synchronized with the waveforms even if the PPT value changes.

In one embodiment, the first synchronization unit may use the ECG data only. In another embodiment, the first and second synchronization units generate an autoregressive model for the estimation of the time instants of the systolic rises. In one embodiment, all the entities of FIG. 17 may be in the central unit, while in another embodiment all the entities may be in the smart sensor. The latter embodiment concerns the above-described spot-checker in which all components necessary for obtaining the blood parameter readings, typically SpO2 readings, are integrated into a single portable device. In other embodiments, the second synchronization unit and possibly also the first synchronization unit may be in the smart sensor. If the second synchronization unit is in the smart sensor, it may receive timing information from the central unit, the timing information being indicative of the LED activation moments.

FIG. 18 illustrates an example of the functional entities of the first synchronization unit 171. In the initial detection phase, the signal samples are supplied to a timing control unit 183 that determines the initial timing information for the first light bursts and supplies the timing information to the second synchronization unit 172. When the actual measurement is started, a differential unit 181 determines the difference values and a timing adjustment unit 182 compares the difference values and adjusts the timing of the light bursts according to the mutual magnitudes of the successive difference values. During the actual measurement, timing control data may also be sent from the timing control unit 183 to the timing adjustment unit. During the measurement, a resynchronization process similar to the initial synchronization may be carried out to maintain synchronization. In one embodiment of the pulse oximeter system, the differential unit 181 and the timing adjustment unit 182 may be in the smart sensor, and the timing control unit 183 in the central unit. The timing control unit may receive ECG signal data for the synchronization of the LEDs.

It is to be noted that FIGS. 17 and 18 illustrate the division of the functionalities of the sensor system in logical sense and in view of the LED synchronization. In a real apparatus the functionalities may be distributed in different ways between the elements or units of the pulse oximeter. That is, the pulse oximeter system may comprise the above functional units only at logical level. Further, in addition to, or instead of the determination of SpO2, the collected photoplethysmographic data may be used to determine any blood parameter for which the signal sections containing the systolic rises provide enough input data.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural or operational elements that do not differ from the literal language of the claims, or if they have structural or operational elements with insubstantial differences from the literal language of the claims.

The invention claimed is:

1. A method for determining blood characteristics of a subject based on photoplethysmographic data, the method comprising:
   estimating time instants of systolic rises in at least one plethysmographic waveform of a subject;
   controlling light emitting elements of a sensor according to the estimated time instants, thereby to collect signal samples from a plurality of plethysmographic waveforms of the subject during the systolic rises; and
   defining at least one desired blood parameter based on the signal samples collected during the systolic rises.

2. The method according to claim 1, wherein the estimating includes
   collecting a sequence of plethysmographic signal data during at least one cardiac cycle;
   determining a time instant of a systolic rise from each of the at least one cardiac cycle, thereby to obtain at least one time instant; and
   estimating the time instants of the systolic rises based on the at least one time instant,
   wherein the collecting, determining, and estimating are performed for one plethysmographic waveform.

3. The method according to claim 1, further comprising
   determining difference values of successive signal samples obtained from one systolic rise, wherein the determining is performed for at least one of the plurality of plethysmographic waveforms; and
   adjusting the estimated time instants according to the difference values.

4. The method according to claim 3, wherein
   the determining includes determining the difference values for at least two of the plurality of plethysmographic waveforms; and
   the defining includes determining a line by linear regression of the difference values, determining the slope of the line, and determining the at least one desired blood parameter based on the slope, in which the at least one desired blood parameter is oxygen saturation.

5. The method according to claim 1, wherein the estimating includes sending test pulse pairs to detect a starting point for each systolic rise.

6. The method according to claim 1, wherein the defining includes applying a Fourier transform to the signal samples collected from at least two of the plurality of plethysmographic waveforms during the systolic rises.

7. A pulse oximeter system for determining blood characteristics of a subject, the pulse oximeter system comprising:
   a sensor comprising light emitting elements;
   a first synchronization unit configured to estimate time instants of systolic rises in at least one plethysmographic waveform of a subject;
   a second synchronization unit configured to control the light emitting elements according to the estimated time instants, thereby to collect signal samples from a plurality of plethysmographic waveforms of the subject during the systolic rises; and a calculation unit configured to define at least one desired blood parameter based on the signal samples collected during the systolic rises.

8. The pulse oximeter system according to claim 7, wherein the first synchronization unit is configured to
collect a sequence of plethysmographic signal data during at least one cardiac cycle for one of the at least one plethysmographic waveform;
determine a time instant of a systolic rise from each of the at least one cardiac cycle, thereby to obtain at least one time instant; and
estimate the time instants of the systolic rises based on the at least one time instant.

9. The pulse oximeter system according to claim 8, wherein the first synchronization unit is configured to receive ECG signal data and calculate a pulse transit time based on the ECG signal data and the sequence of plethysmographic signal data.

10. The pulse oximeter system according to claim 8, wherein
the first synchronization unit is configured to receive ECG signal data, detect R peaks from the ECG signal data, and indicate time instants of the R peaks to the second synchronization unit; and
the second synchronization unit is configured to switch the light emitting elements on at a given rate for a given time period after each R peak.

11. The pulse oximeter system according to claim 7, wherein the first synchronization unit is further configured to
determine, for at least one of the plurality of plethysmographic waveforms, difference values of successive signal samples obtained from one systolic rise; and
adjust the estimated time instants based on the difference values.

12. The pulse oximeter system according to claim 11, wherein
the first synchronization unit is configured to determine the difference values for at least two of the plurality of plethysmographic waveforms; and
the calculation unit is configured to determine a line by linear regression of the difference values, determine the slope of the line, and determine the at least one desired blood parameter based on the slope, in which the at least one desired blood parameter is oxygen saturation.

13. The pulse oximeter system according to claim 7, wherein the system is configured to send test pulse pairs to detect a starting point for each systolic rise.

14. The pulse oximeter system according to claim 7, wherein the calculation unit is configured to apply a Fourier transform to the signal samples collected from at least two of the plurality of plethysmographic waveforms during the systolic rises.

15. A pulse oximeter sensor for collecting plethysmographic data, the pulse oximeter sensor comprising:
light emitting elements; and
a synchronization unit configured to receive timing information indicative of time instants of systolic rises in plethysmographic waveforms of a subject and to control the light emitting elements according to the time instants, thereby to collect signal samples from the plethysmographic waveforms during the systolic rises.

16. The pulse oximeter sensor according to claim 15, further comprising a further synchronization unit configured to estimate the time instants of the systolic rises in at least one of the plethysmographic waveforms.

17. The pulse oximeter sensor according to claim 16, wherein the further synchronization unit is configured to
collect a sequence of plethysmographic signal data during at least one cardiac cycle for one of the plethysmographic waveforms;
determine a time instant of a systolic rise from each of the at least one cardiac cycle, thereby to obtain at least one time instant; and
estimate the time instants of the systolic rises based on the at least one time instant.

18. The pulse oximeter sensor according to claim 17, wherein the further synchronization unit is configured to receive ECG signal data, detect R peaks from the ECG signal data, and estimate the time instants of the systolic rises based on the R peaks.

19. The pulse oximeter sensor according to claim 16, wherein the further synchronization unit is further configured to
determine, for at least one of the plethysmographic waveforms, difference values of successive signal samples obtained from one systolic rise; and
adjust the estimated time instants based on the difference values.

20. The pulse oximeter sensor according to claim 15, wherein the sensor is configured to send test pulse pairs to detect a starting point for each systolic rise.

* * * * *